United States Patent [19]

Anderson

[11] 4,184,892

[45] Jan. 22, 1980

[54] ORGANIC DIGESTER APPARATUS AND METHOD

[76] Inventor: Jay Anderson, P.O. Box 585, Elkhart, Ind. 46514

[21] Appl. No.: 812,144

[22] Filed: Jul. 1, 1977

Related U.S. Application Data

[62] Division of Ser. No. 595,176, Jul. 11, 1975, Pat. No. 4,046,551.

[51] Int. Cl.² .......................... B08B 9/00; B08B 9/04; B08B 3/00
[52] U.S. Cl. ........................................ 134/24; 134/23; 134/114
[58] Field of Search ................ 134/23, 22 R, 24, 114, 134/167 R, 177, 175, 180, 181, 34; 23/259.1; 210/520, 513, 4, 12; 239/208, 209, 225

[56] References Cited

U.S. PATENT DOCUMENTS

| | | | |
|---|---|---|---|
| 2,748,744 | 6/1956 | Kalinske | 210/520 |
| 2,768,136 | 10/1956 | Wright | 210/D9 |
| 3,114,622 | 12/1963 | Hardy | 71/9 |
| 3,298,670 | 1/1967 | Crom | 210/76 |
| 3,969,133 | 7/1976 | McTighe et al. | 134/24 |
| 3,985,572 | 10/1976 | Peterman | 134/34 |

FOREIGN PATENT DOCUMENTS 1193454 6/1970 United Kingdom ..................... 239/140

Primary Examiner—Joseph Scovronek
Assistant Examiner—Chris Konkol
Attorney, Agent, or Firm—Wendell E. Miller

[57] ABSTRACT

A method is provided for washing the inside of an organic digester of the type having a rotatable roof member. The method includes supporting the roof member, with pressurized gas excluding oxygen, rotating the roof member, spraying water on the interior walls of the digester, and observing the washing process.

7 Claims, 13 Drawing Figures

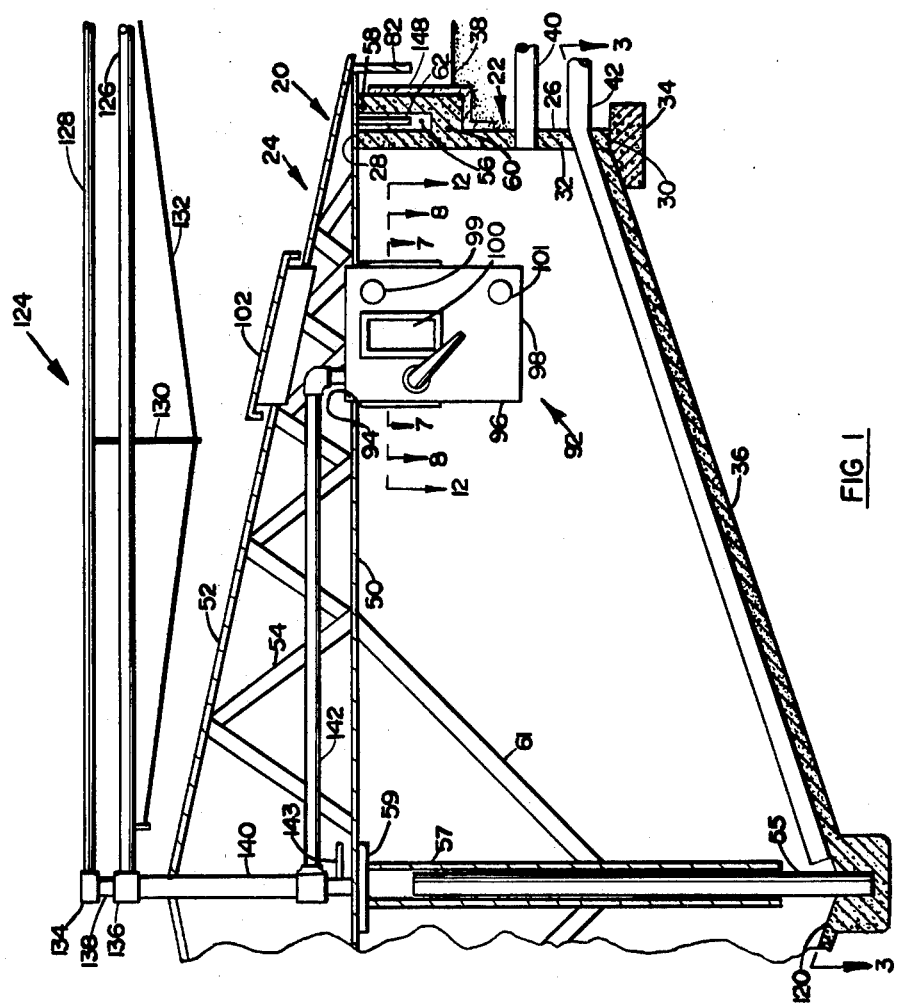

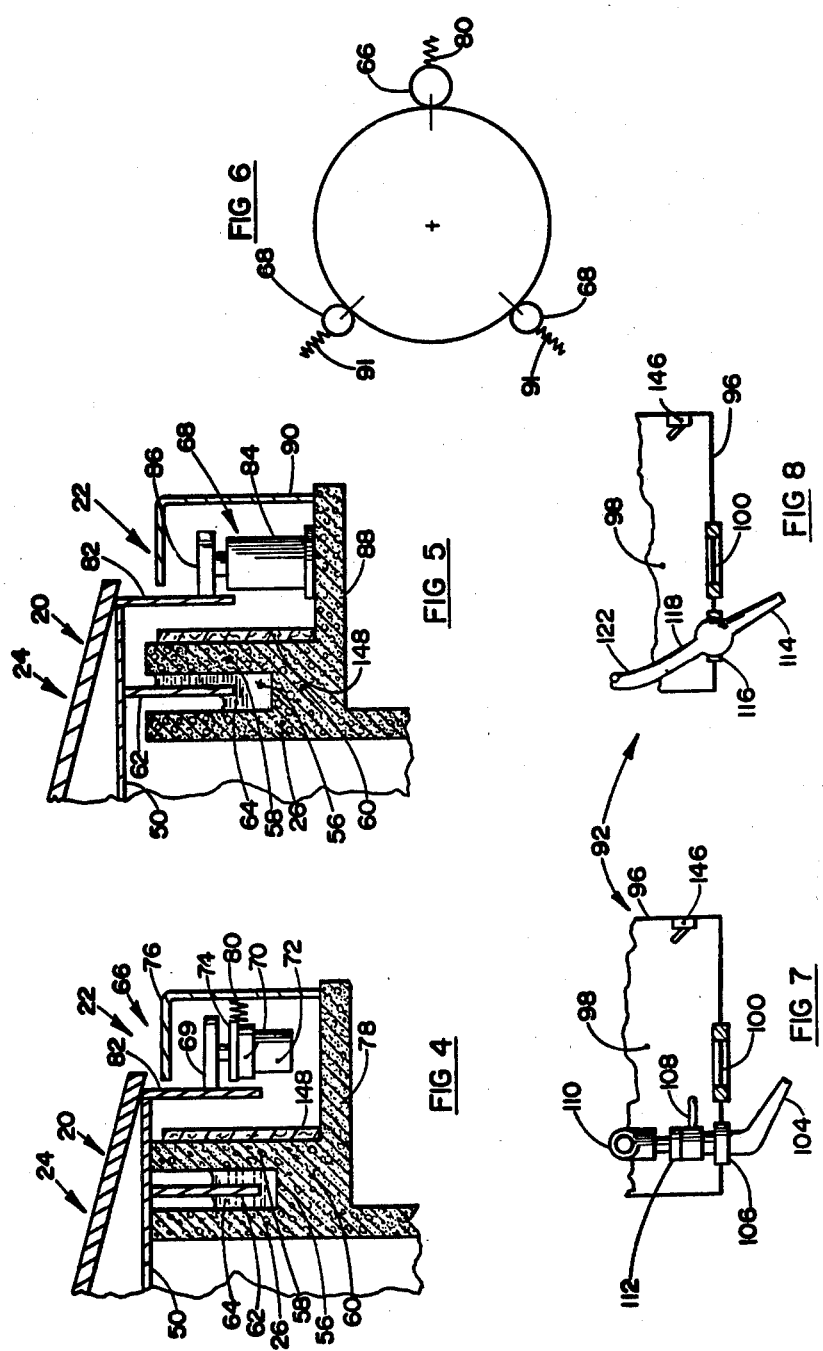

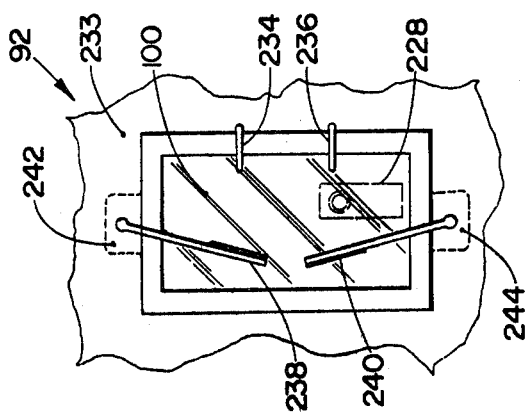
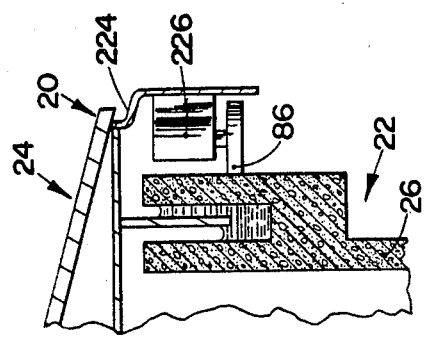
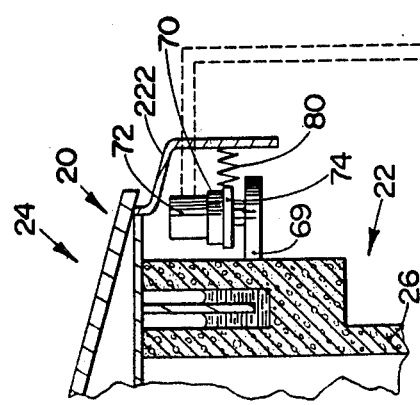
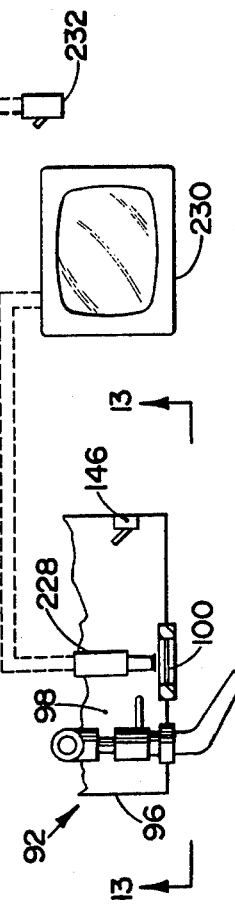

ORGANIC DIGESTER APPARATUS AND METHOD

This is a division of application Ser. No. 595,176, filed July 11, 1975, now U.S. Pat. No. 4,046,551.

BACKGROUND OF THE INVENTION

1. Field of the Invention

This invention relates generally to organic digesters and more particularly to an improved organic digester apparatus and to an improved method of producing liquid fertilizer and methane gas from organic materials.

2. Description of the Prior Art

The method of manufacturing natural fertilizer and methane gas from organic material by anaerobic digestion is well-known and products sold from this process include a granular fertilizer which is sold under the name Milorganite. The typical method generally includes depositing organic material into a closed container and maintaining the temperature of the organic material at a temperature range of 90 degrees to 105 degrees Fahrenheit for a period of 42 to 60 days.

The typical apparatus has generally included a spherically shaped digester tank and removable roof member. The types of apparatus and methods previously used include the batch type digester in which a quantity of organic material is placed in the digester and retained in the digester until completion of the digesting process, and the displacement type digester in which organic material is continuously, or continually, deposited in the digester, and liquid fertilizer is continuously, or continually, removed from the digester.

The problem which is inherent with the batch type digester is that organic material can be deposited in the digester only after completion of the digesting cycle and the removal of completed fertilizer from the digester. The problem which is inherent with the displacement type digester is that incompletely digested material is mixed with the completely digested organic material which has been transformed into liquid fertilizer; so that, when the liquid fertilizer is removed from the displacement type digester, rather than being pure fertilizer, it is contaminated with incompletely digested organic material.

SUMMARY OF THE INVENTION

In accordance with the broader aspects of this invention, there is provided an organic digester apparatus which includes a digester tank and a removable roof member. The digester tank is of generally cylindrical shape and includes a conical bottom member. The digester tank is also provided with a circumferential sealing well which is displaced radially outward from the digester tank. The removable roof member includes a circumferential sealing skirt depending from the lower surface of the roof member and extending downward into the sealing well. A liquid in the sealing well provides a gas-tight seal between the inside of the digester tank, which contains methane gas, and the outside atmosphere.

The apparatus includes control means for controlling the volume of gas within the digester tank so that the roof member is floated by gas pressure above the digester tank within predetermined, or adjustably predetermined, upper and lower limits. An electric motor drive is provided between the roof member and the digester tank to controllably rotate the roof member, very small power being required to rotate the roof member since it is floating on the methane gas.

An observation capsule is provided in the roof member and depends therefrom downward into the digester tank. The observation capsule is provided with windows for observing the inside of the digester walls, with a source of water and directable nozzle for washing the inside of the digester walls, and with an electrical switch for selectively controlling the rotation of the roof member as the walls of the digester are washed and inspected.

In a preferred embodiment some of the apparatus includes four digesters, the four digesters being a collecting digester, a first stage digester, a second stage digester, and a final stage digester. The apparatus further includes liquid and gas handling systems.

The liquid handling system includes a slurry pump, valves, and conduits for depositing, transferring, and removing liquid materials. The liquid handling system further includes a meter for measuring the quantity of liquid fertilizer removed from the final stage digester.

The gas handling system includes a control device for maintaining the gas volume in the digester tank at a volume which maintains the roof member between upper and lower predetermined limits, a gas meter for measuring the volume of gas removed from each of the digester tanks, a storage tank for storing the gas at an increased pressure level, and a compressor which is driven by a natural gas type of internal combustion engine for compressing the gas into the storage tank.

The method includes periodically depositing organic material into the collecting digester, transferring the organic material from the collecting digester to the first stage digester, transferring the organic material from the first stage digester to the second stage digester, transferring the organic material from the second stage digester to the final stage digester, holding the organic material for at least seven days in the last three mentioned digesters, removing liquid fertilizer from the final stage digester, and removing methane gas from all of the aforesaid digesters.

It is a first object of this invention to provide a digester tank for organic materials which includes a liquid seal between the digester tank and the roof member.

It is a second object of this invention to provide means for rotating the roof member of an organic digester apparatus.

It is a third object of this invention to provide control means for controlling the volume of methane gas within an organic digester apparatus to maintain the roof member of the digester apparatus in a floating relationship above the digester tank within predetermined distances.

It is a fourth object of this invention to provide an observation port in the roof member of the digester apparatus and means for rotating the roof member; so that a radially displaced observation port is sufficient for viewing the entire surface of the digester as the roof member is rotated.

A fifth object of this invention is to provide an observation capsule depending from the roof member of the digester and displaced from the center thereof, the observation capsule being of sufficient size to house a human observer.

It is a sixth object of the present invention to provide an observation port in the roof member of a digester apparatus, to provide a means for rotating the roof member, and to provide means for selectively directing a jet of water against the inside surfaces of the digester tank so that the inside of the digester tank can be effectively washed without removing the roof member.

It is a seventh object of this invention to provide control means within an observation capsule which depends from the roof member, for selectively controlling the rotation of the roof member.

It is an eighth object of the present invention to provide a step method for the digesting of organic material anaerobic for the producing of liquid fertilizer and methane gas.

It is a ninth object of the present invention to provide apparatus for the accomplishing of the steps of the step digesting process.

The abovementioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

In the drawings:

FIG. 1 is a partial front elevation, in cross-section, of the digester tank of the present invention;

FIG. 2 is an enlarged partial cross-section of the bottom member of the digester tank of FIG. 1;

FIG. 3 is a cross-sectional view taken substantially as shown by section line 3—3 of FIG. 1;

FIG. 4 is an enlarged and cross-sectioned view of a portion of the digester tank of FIG. 1, showing the circumferential sealing well thereof, being taken at a circumferentially displaced location from that of FIG. 1 and showing the electric motor and drive wheel unit for rotating the roof member;

FIG. 5 is an enlarged partial and cross-sectioned view of the digester apparatus of FIG. 1, taken at a second circumferentially displaced location from that of FIG. 4, and showing a guide mechanism;

FIG. 6 is a top plan view of the roof member, showing, diagrammatically, the preferred positions for the drive wheel unit and the guide mechanisms;

FIG. 7 is an enlarged and partial cross-section of the observation capsule of FIG. 1 taken substantially as shown by section line 7—7 of FIG. 1;

FIG. 8 is a partial and enlarged cross-section of the observation capsule of FIG. 1 taken substantially as shown by section line 8—8 of FIG. 1;

FIG. 10 is an enlarged and cross-sectioned view of a portion of the digester tank of FIG. 1, showing the circumferential sealing well thereof, being taken at a circumferentially displaced location from that of FIG. 1, and showing an alternate electric motor and drive wheel unit from that of FIG. 4;

FIG. 11 is an enlarged partial and cross-sectioned view of the digester tank of FIG. 1, taken at a second circumferentially spaced location from that of FIG. 10, and showing an alternate embodiment of the guide mechanism from that which is shown in FIG. 5;

FIG. 12 is an enlarged and partial cross-section of the observation capsule of FIG. 1 taken substantially as shown by section line 12—12 of FIG. 1; and FIG. 13 is an enlarbged and partial view of the observation capsule of FIG. 1 taken substantially as shown by view line 13—13 of FIG. 12.

DESCRIPTION OF THE PREFERRED EMBODIMENT

Figure 9:
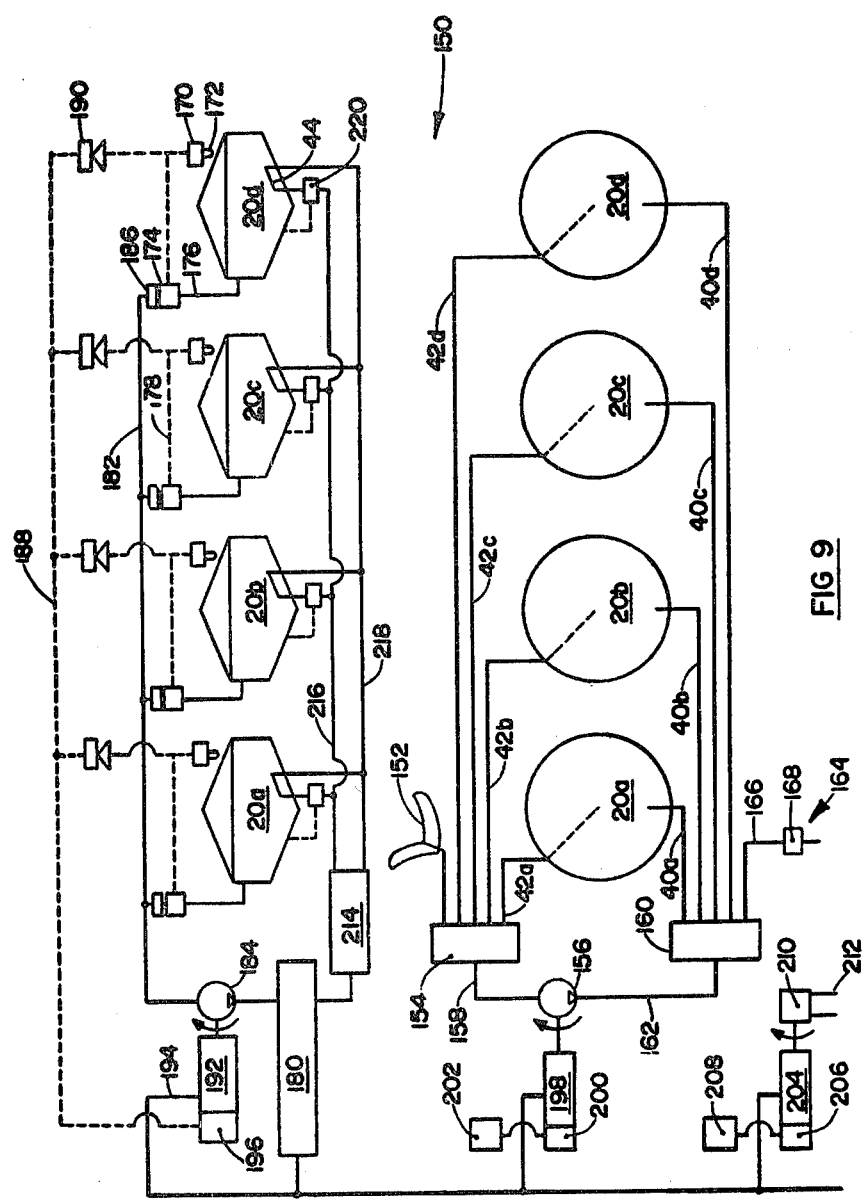
FIG. 9 is a schematic drawing of an organic digester system, including a plurality of organic digesters, for accomplishing the step digesting process of the present invention.

Referring now to the drawings, and particularly to FIG. 1, a digester or digester apparatus 20 includes a digester tank 22 and a removable roof member 24. The digester tank 22 includes a circular wall member or circular wall means 26 which is preferably a cylindrically shaped member. The circular wall member 26 includes an upper end 28, a lower end 30, and an inside wall 32. The circular wall member 26 rests upon a circular, ring-shaped footing 34. The footing 34 also supports a conically shaped bottom member 36. The circular wall member 26, the footing 34, and the bottom member 36 are preferably formed of reinforced concrete. A portion of the cylindrically shaped member 26, and the bottom member 36, are placed below grade as shown by grade line 38.

The digester tank 22 includes a slurry filling conduit 40 and a slurry removing conduit 42.

Referring now to FIGS. 1–3, the bottom member 36 includes heating conduit means 44 which is preferably arranged in a spiral configuration in the bottom member 36 and which may include parallel connected branches such as branches 46 and 48. The branches 46 and 48 are connected in parallel to increase the volume flow of hot water which can be circulated through the heating conduit means 44.

Referring again to FIG. 1, the removable roof member 24 includes a gas-impervious plate 50, a conically shaped roof 52, and trusses 54. The digester tank 22 includes an upstanding guide post 55 which is fastened to the bottom member 36, and a guide tube 57 which is fastened to a reinforcing plate 59 and to the plate 50 and which telescopically slides over the guide post 55 to provide a guide means for the roof member 24; so that the roof member raises uniformly on all sides and remains radially centered. Struts 61 provide rigidity between the roof member 24 and the guide tube 57.

Referring now to FIGS. 1, 4, and 5, the digester apparatus 20 includes liquid seal means for providing a gas-tight seal between the digester tank 22 and the roof member 24. The liquid seal means includes a circumferential sealing well 56 which is provided radially outward from the circular wall member 26 and proximal to the upper end 28 thereof. The circumferential sealing well 56 comprises a circumferential space between a circumferential wall 58 and the circular wall member 26. A well bottom portion 60 cooperates with the circumferential wall 58 to connect the wall 58 to the circular wall member 26.

The liquid seal means further includes a circumferential sealing skirt 62 which is attached to the plate 50 and which depends therefrom into the sealing well 56. A liquid 64 provides a gas-tight seal between the digester tank 22 and the roof member 24 and allows both rotary motion and vertical movement between the roof member 24 and the digester tank 22.

Referring now to FIGS. 1, 4, 5, and 6, the digester apparatus of FIG. 1 includes a drive means or electric motor and drive wheel unit 66 of FIG. 4 and a guide means or guide mechanism 68 of FIG. 5.

Referring now to FIG. 4, the electric motor and drive wheel unit 66 includes a drive wheel 69 which is rotatably attached to a gear unit 70 and the gear unit 70 is drivingly attached to an electric motor 72. The gear unit 70 is attached to a pivot arm 74 which is in turn attached to a housing 76, the housing 76 being attached to a base 78 which is an integral part of the bottom portion 60. A spring 80 is interposed between the housing 76 and the pivot arm 74 to resiliently force the drive wheel 69 against a rain-precluding or second circumferential skirt 82 which is attached to the roof member 24 and which depends therefrom in radially outward spaced location from the circumferential sealing skirt 62. Thus the electric motor 72, the gear unit 70, and the drive wheel 69 provide a drive means or rotating means for rotating the roof member 24.

Referring now to FIGS. 5 and 6, a pair of guide means or guide mechanisms 68 are located at two circumferentially spaced positions around the second circumferential skirt 82 as shown in FIG. 6 and provide means for radially guiding the roof member 24 and for balancing the radial force which is imposed by rotating means 66 of FIG. 4. The guide means 68 includes a pedestal, shaft, and bearing assembly 84, a guide roller 86, a base 88 which is an integral portion of the well bottom portion 60, and a housing 90. Optionally, the guide mechanisms 68 may be omitted because of the radial guiding that is provided by the post 55 and the guide tube 57; or optionally, the guide mechanisms may be spring loaded by springs 91 (FIG. 6) to provide resilient radial balancing for the radial force of the spring 80 of the drive means 66.

Referring now to FIGS. 1, 7, and 8, the digester apparatus 20 includes an observation capsule 92 which is inserted into an opening 94 in the plate 50 and which is sealably attached to the plate 50. The observation capsule 92 includes capsule wall means 96 and a floor 98, it being understood that the observation capsule 92 is of sufficient size for receiving a human observer.

The observation capsule 92 includes an observation port or observation port means 100 which comprises a plurality of windows and includes electric lights 99 and 101 for lighting of the interior of the digester tank 22. Access to the observation capsule 92 is by way of a hatch 102 in the conically shaped roof 52.

Referring now to FIGS. 1 and 7, a water nozzle 104 is inserted through the capsule wall means 96 of the observation capsule 92 and is mounted to the capsule wall means 96 by a sealing swivel 106. Inside the observation capsule 92, a handle 108 is provided to rotatably direct the nozzle 104. Intermediate of the handle 108 and water conduit means 110, a swivel fitting 112 is provided to allow the free rotation of the nozzle 104 by the handle 108.

Referring now to FIGS. 1 and 8, an alternate design includes a nozzle 114 which is sealably mounted in the capsule wall means 96 by the use of a universal swivel 116. The nozzle 114 includes a handle portion 118 for controllably directing fluid from the nozzle 114 against the inside walls 32 of the circular wall member 26 and against the inside bottom surface 120 of the bottom member 36. The nozzle 114 is supplied with water from a flexible conduit means 122 which allows the universal swiveling of the nozzle 114.

Referring again to FIGS. 1, 7, and 8, pressurized water is supplied to the nozzle 104 of FIG. 7 or to the nozzle 114 of FIG. 8 by way of a boom 124. The boom 124 includes a water conduit 126, an electrical conduit 128, a strut 130, a truss member 132, and swivel fittings 134 and 136.

The boom 124 also includes an inner post 138 which is attached at the bottom end thereof to the plate 50, and an outer post 140 which is attached to the conically shaped roof 52. The inner post 138 is sealably inserted into the swivel fitting 136; so that water from the water conduit 126 flows between the inner post 138 and the outer post 140 and then into a water conduit 142. The water conduit 142 is then either connected to the water conduit means 110 of FIG. 7 or to the flexible conduit means 122 of FIG. 8. The swivel fitting 134 provides for relative rotary motion between the boom 124 and the roof member 24 and for the transmission of electrical power from the electrical conduit 128 to an electrical conduit 143. In like manner, the swivel fitting 136 provides for relative rotary motion between the boom 124 and the roof member 24 and for the transmission of pressurized water from the conduit 126 to the conduit 142.

Referring now to FIGS. 4, 7, and 8, an electrical switch 146 is provided in the observation capsule 92 and is connected by wires (not shown) to the rotating means 66 of FIG. 4 by means of the electrical conduit 128 of FIG. 1 to provide manually selective control of the rotating means 66.

Referring again to FIGS. 4 and 5, a layer of insulating material 148 is attached to the outer surface of the circumferential wall 58 to restrict the flow of heat from the liquid 64, through the circumferential wall 58, to a cold atmosphere thereby effectively preventing freezing of the liquid 64.

Referring now to FIG. 10, in an alternate embodiment of the present invention, the electric motor 72 and the gear unit 70 are pivotally attached to a drive housing 222 by the pivot arm 74, the drive housing 222 being attached to the roof member 24 and replacing a portion of the second circumferential skirt (FIG. 4). The drive wheel 69, which is driven by the electric motor 72 and the gear unit 70 is resiliently urged by the spring 80 into operative engagement with the periphery of the digester tank 20.

Referring now to FIG. 11, the guide roller 86 is rotatably mounted to a roller housing 224 by a pedestal, shaft, and bearing assembly 226 in a location wherein the drive roller 86 operatively engages the periphery of the digester tank 22. The roller housing 224 is connected to the roof member 24 and replaces a portion of the second circumferential skirt 82. In like manner as with the embodiment of FIG. 5, a pair of the guide rollers 86 may be located as shown in FIG. 6 and may be either rigidly mounted as shown in FIG. 11 or may be spring loaded by the springs 91 of FIG. 6.

Referring now to FIG. 12, in an alternate embodiment, the observation capsule 92 is provided with a video camera 228 for remotely viewing the inside of the digester tank 22. The video camera 228 is connected to a video monitor 230 which is located externally of the digester apparatus 20 and at any proximal or distal location as desired. A roof rotating control switch 232 is provided proximal to the video monitor 230, is operatively connected to the electric motor 72 (FIG. 10), and is effective to selectively control the rotation of the roof member 24.

Referring now to FIGS. 12 and 13, and more particularly to FIG. 13, the window 100 includes an inside surface 233 which is proximal to the inside of the digester tank 22 and which is distal from the inside of the observation capsule 92. The observation capsule 92 is provided with windshield washer means which includes jets 234 and 236 which are adapted to spray water or other cleaning fluid onto the inside surface 233 of the window 100. The observation capsule 92 is also provided with windshield wiper means which includes a pair of wiper blades 238 and 240 which are operatively connected to and driven by a pair of wiper motors 242 and 244.

Referring now to FIG. 9, an organic digester system 150 includes a plurality of the digesters or digester apparatus 20 such as has been previously described. Each digester apparatus 20 is diagrammatically represented both from front elevation and top views, it being understood that the separate representations do not represent separate digesters, but instead provide a means for more clearly depicting the connections of the various conduits and other components.

The organic digester system includes a collecting digester 20a, a first stage digester 20b, a second stage digester 20c, and a final stage digester 20d.

The slurry conduit and pumping system includes a receiving station 152 which is connected to a valve and header assembly 154, and the header system 154 is connected to a slurry pump 156 by a conduit 158. The valve and header assembly 154 is connected to the digesters 20a-20d by slurry removing conduits 42a-42d respectively. In like manner, the slurry pump 156 is connected to a valve and header assembly 160 by conduit 162; and the valve and header assembly 160 is connected to the digesters 20a-20d by slurry filling conduits 40a-40d respectively to deposit organic material into the respective digesters. A fertilizer removal station 164 includes a conduit 166 which is connected to the valve and header assembly 160 and a bulk fluid meter 168 which is interposed into the conduit 166 and which provides a means for measuring the quantity of liquid fertilizer that is discharged from the final stage digester 20d.

Referring now to the portion of FIG. 9 which depicts the gas handling system, each of the digesters 20 is equipped with a roof height sensing switch 170 which is adapted to provide or to break an electrical connection depending upon predetermined upper and lower positions of the roof member 24, the position sensing function of the switch 170 being depicted by a finger 172. A solenoid valve 174 is connected to each digester apparatus 20 at a point above the slurry level therein by a gas conduit 176. Each solenoid valve 174 is connected to a respective one of the roof height sensing switches 170 by an electrical conduit 178. Each solenoid valve 174 is further connected to a gas receiving tank 180 by conduits 182 and by a gas compressor 184. Interposed into the conduits 182 is a gas volume meter 186 for the measuring of the methane gas which is produced by each digester apparatus 20.

Each of the roof height sensing switches 170 is connected to an engine starting conductor 188 by a diode 190 so that the engine starting conductor 188 is energized by any one of the switches 170.

The gas compressor 184 is operated by an internal combustion engine 192 which is operated by methane gas received from the tank 180 through a conduit 194. The engine 192 is equipped with a battery and starter unit 196 which is in turn connected to the engine starting conductor 188. Thus, in accordance with predetermined roof heights of the roof member 24, the switches 170 and the solenoid valves 174 are effective to cooperate with the gas compressor 184 and the gas receiving tank 180 to remove methane gas from any one of the digester apparatus 20 to maintain the height of the respective roof members between predetermined upper and lower limits.

Referring again to FIG. 9, the slurry pump 156 is driven by an internal combustion engine 198 which is likewise furnished with gas from tank 180 and conduit 194 and which also includes a battery and starter unit 200. The battery and starter unit 200 is provided with a manual control station 202 for selectively starting the engine 198 and operating the slurry pump 156.

The system 150 includes an internal combustion engine 204, a battery and starter unit 206, and a starter control station 208. The engine 204 is connected to an alternator 210 to provide electrical power in electrical conductors 212.

The organic digester system 150 further includes a gas fired water boiler 214 which receives methane gas from the tank 180, which burns the methane gas, and which heats water for circulation to the heating conduit means 44 in each of the digester tanks 22. The water boiler 214 is connected to each of the digester apparatus 20 by a supply conduit 216 and a return conduit 218. Interposed between the conduits 216 and each of the heating conduit means 44 of each digester apparatus 20 is a thermostatically controlled water valve 220 for the maintaining of the slurry temperature between predetermined limits.

From the foregoing description it can be seen that the organic digester system 150 manufactures liquid fertilizer and methane gas, that this methane gas is used for powering the engine 192 which drives the gas compressor 184, for powering the engine 198 which drives the slurry pump 156, and for powering the engine 204 which drives the alternator 210. Thus the system 150 is effective to provide gas and electrical power for operation of the step digester system 150 and is also effective to provide additional gas and electrical power for other uses on a farm.

In operation of the system, referring again to FIG. 9, manure, fecal excrement, or other organic material is placed into the receiving station 152, and if necessary, mixed with water to obtain a consistency which can be pumped through the various conduits. The valve and header assemblies 154 and 160 are manually actuated to interconnect the receiving station 152 with the collecting digester 20a by way of the slurry pump 156; and the organic material in the receiving station 152 is deposited in the collecting digester 20a. The collecting digester 20a may be completely filled during a period of one day or less or it may be filled over a period which is equal to the cycle time in each of the other digesters 20.

The organic material in the collecting digester 20a is heated to the temperature range 90 degrees to 105 degrees Fahrenheit by the heating conduit means 44 (FIGS. 2 & 3); but if, during cold weather, the temperature of organic material in the organic digester 20a falls below the 90 degree Fahrenheit temperature, due to the introduction of cold organic material, the process is not harmed; since this same organic material will subsequently be maintained within the prescribed temperature limits in the succeeding digesters. Thus, it can be seen that the time, temperature, and method of introduction of the organic material into the collecting digester 20a does not affect the quality of the fertilizer being manufactured.

The organic material in the collecting digester 20a is subsequently transferred to the first stage digester 20b, from the first digester 20b to the second stage digester 20c, and then to the final stage digester 20d, this same quantity of organic material being held in each digester for a period of at least seven days. Preferably, this quantity of organic material is held in each digester 20 for a period of fifteen days; so that any given quantity or batch of organic material is in the digesters 20 for a total of at least forty-five days plus whatever time this same quantity of organic material might have been in the collecting digester 20a.

Transferring of organic material from one of the digesters 20 to another of the digesters 20 is accomplished by actuating the valve and header assemblies 154 and 160 to interconnect respective ones of the conduits 42 and 40 so that the organic material is drawn from one of the conduits 42, through the slurry pump 156 and through one of the conduits 40 to another of the digesters 20.

It should be understood that, at any given time, there will be different batches of organic material being processed in each of the digesters; so that the process is a step process with different batches of organic material being in respective ones of the steps of the step digesting process.

For the removal of completely processed organic material from the final stage digester, that is, for the removal of liquid fertilizer from the final stage digester 20d, the valve and header assemblies 154 and 160 are first actuated to pump liquid fertilizer from the final stage digester 20d through the conduit 42d, through the pump 156, and through the conduit 40a to the collecting digester 20a. This process is used to flush the conduits 158 and 162 and thereby to completely remove undigested organic material from these conduits. Then the valve and header assembly 160 is actuated to interconnect the conduit 42d with the conduit 166; and thereby to pump liquid fertilizer from the final stage digester 20d through the conduit 166 and through the bulk fluid meter 168 into a tank truck (not shown).

Referring now to FIGS. 1 and 9, methane gas will be produced in various quantities in all of the digesters 20. The digester apparatus 20 of FIG. 1, which is typical of all of the digesters of FIG. 9, is designed so that the roof member 24 raises and lowers to provide a storage vessel for the gas which is produced in the digester apparatus 20. This gas is maintained at a pressure of three to six inches of water, the pressure being controlled by the weight of the removable roof member 24, and, if necessary, the addition of weights (not shown) to the conically shaped roof 52. The height of the roof is controlled by the volume of gas within the digester apparatus 20, and the volume of gas within the digester apparatus 20 is controlled by the roof height sensing switch 170 and the solenoid valve 174 of FIG. 9.

The seal between the roof member 24 and the digester tank 22 is maintained by the liquid 64 in the circumferential sealing well 56. The liquid 64 may be water, water plus an antifreeze, or oil. When there is no gas pressure in the digester apparatus 20, the level of the liquid 64 will be as shown in FIG. 4, but with gas pressure within the digester apparatus 20, the liquid levels on opposite sides of the circumferential sealing skirt 62 will be as shown in FIG. 5.

Referring again to FIG. 9, it is desirable to intermittently agitate the slurry during the digesting process. The system 150 of the present system utilizes the slurry pump 156 to recirculatingly pump slurry from any of the digesters and the respective one of the conduits 42 back into the same one of the digesters 20 via the respective one of the conduits 40. Thus the system 150 includes an agitating means which comprises the slurry pump 156.

When any of the digesters 20 is emptied of slurry or liquid fertilizer, it is necessary to replace the volume of liquid that is removed with a sufficient volume of gas or air to prevent an excessively high vacuum in the digester 20 which could possibly collapse the roof member 24. Preferably, air is excluded from the digester 20, and gas from the tank 180 is returned to the digester 20 to maintain the gas pressure in each of the digesters 20 at three to six inches of water and to maintain the respective ones of roof members 24 in suspended positions. Thus, when a digester 20 is emptied of slurry or liquid fertilizer, the roof member 24 is easily rotated for the washing process because it is floated on the gas inside the digester 20.

In a typical system, each digester apparatus 20 will be 50 feet in diameter and the gas receiving tank 180 will be of 30,000 gallon capacity.

The digesting method includes: depositing organic material into the collecting digester 20a at any time during a period which is equal to the retention time in each of the succeeding digesters, transferring the organic material successively to the succeeding digester 20, and retaining each batch or organic material in each of the digesters 20b–20d for a period of at least seven days, but preferably fifteen days.

Referring to FIG. 1, the method of washing the digester apparatus includes: observing the inside walls 32 and the inside bottom surface 120 through the observation port means 100, controllably rotating the roof member 24 by manual actuation of the electrical switch 146 (FIGS. 7 & 8), and manually directing a jet of water from the nozzle 104 (FIG. 7) or the nozzle 114 (FIG. 8) against the inside wall 32 and the inside bottom surface 120.

In summary, the present invention provides a liquid seal means between a digester tank 22 and a roof member 24 so the roof member 24 may be raised and lowered or rotated without breaking the gas seal between the digester tank 22 and the roof member 24 which is provided by the liquid seal means. Being able to raise and lower the roof member 24 provides a change in volume within the digester apparatus 20 for the effective storing of the methane gas which is being produced; whereas, being able to rotate the roof member 24 allows the complete inspection of the inside walls 32 and the inside bottom surface 120 by a single window or observation port means 100 which is radially displaced from the center of the roof member 24. In addition, the floating of the roof member 24 on the methane gas is effective to reduce the friction between roof member 24 and the digester tank 22 for rotation of the roof member 24 by very low power. Further, the ability to rotate the roof member 24 makes it possible to wash the inner surfaces of the digester tank 22 by a manually directable water nozzle mounted in each of the roof members 24 in a position radially displaced from the center thereof. Further, in the preferred configuration, the digester apparatus 20 includes the observation capsule 92 from which the operator can observe the washing process and direct the water from the nozzle 104, or the nozzle 114 (FIGS. 7 or 8) against the inside wall 32 and the inside bottom surface 120.

The present invention allows the introduction of organic material into the collecting digester 20a at any time, in any quantity, and at any temperature, without affecting the digesting process of the system or the quality of the fertilizer being produced.

That is, fresh manure is slightly acid but changes to be slightly alkaline during the anaerobic digesting process. Thus, the addition of fresh manure, into a digester in which the complete digesting process is performed, would interfere with the digesting process by unbalancing the pH of the slurry. However, in the present invention, the step digesting apparatus and method prevent fresh manure from being introduced into any digester except for the collecting digester and the first stage digester; and no organic material is deposited into the first stage digester except after it has been emptied. Thus, the pH of the last three digesters cannot be upset, the total time in the last three digesters is sufficient to completely digest the organic material, and so high quality fertilizer is produced without regard to the times of depositing manure into the collecting digester and without regard to the quantities of manure which is deposited therein at the time of each deposit.

In like manner, the introduction of cold manure into the collecting digester will not affect the operation of the process because the organic material is completely digested in the last three digesters without regard to whatever digesting may have occurred in the collecting digester.

Further, the present invention produces methane gas for the heating of the water and for maintaining the temperature of the organic material in the digester, for operating gas engines for pumping of slurry and gas, for operating a gas engine to produce electricity for use on the farm, and for producing additional gas and electricity for use in heating, lighting, and powering the farm. The primary product of the system, which is high quality organic fertilizer, is, as generally known, highly superior to chemical fertilizer for its long-range effects on the soil.

As an additional benefit, stream pollution from the run-off of animal manure is prevented and obnoxious odors are effectively reduced so that the ecology is enhanced. In short, the system of the present invention both saves energy and improves the ecology.

While there have been described above the principles of this invention in connection with specific apparatus and specific method, it is to be clearly understood that this description is made only by way of an example and not as a limitation to the scope of the invention.

What is claimed is:

1. A method of washing inside surfaces of an organic digester of the type having both a wall member and a movable roof member, which method comprises:
    (a) maintaining liquid between the wall member and the roof member, thereby maintaining a gas-tight seal therebetween, and thereby maintaining the exclusion of oxygen from the digester;
    (b) supporting the roof member with means which comprises pressurized gas;
    (c) removing substantially all organic material from the digester; and
    (d) directing water against the inside surfaces of the digester.

2. The method of claim 1 in which said wall member is circular and said roof member is rotatable and said washing method further comprises rotating said roof member.

3. The method of claim 1 in which said supporting step comprises maintaining pressurized methane gas inside the digester.

4. The method of claim 2 in which said rotating step further comprises reducing rotational power requirements; and
    said reducing step comprises supporting the roof member with pressurized methane gas.

5. The method of claim 2 in which said supporting step comprises maintaining pressurized methane gas inside the digester;
    said directing step comprises manually directing; and
    said rotating step comprises reducing rotational power requirements by said maintaining of pressurized methane gas in said digester.

6. The method of claim 2 in which said rotating step comprises:
    (a) radially guiding the roof member; and
    (b) applying a rotating force to the roof member.

7. The method of claim 6 in which said rotating force applying step further comprises:
    (a) fixedly positioning, with respect to one of the members, an electric motor and drive wheel unit;
    (b) engaging the drive wheel with the other member; and
    (c) rotating the drive wheel by the electric motor.

* * * * *